United States Patent [19]

Dallas

[11] Patent Number: 4,469,440
[45] Date of Patent: Sep. 4, 1984

[54] SHORT-EXPOSURE TOMOSYNTHESIS APPARATUS FOR THE FORMATION OF LAYER IMAGES WITH A LOW ARTEFACT-CONTENT

[75] Inventor: William J. Dallas, Hamburg, Fed. Rep. of Germany

[73] Assignee: U.S. Philips Corporation, New York, N.Y.

[21] Appl. No.: 330,636

[22] Filed: Dec. 14, 1981

[30] Foreign Application Priority Data

Dec. 19, 1980 [DE] Fed. Rep. of Germany ....... 3047889

[51] Int. Cl.³ .............................................. G06K 9/58
[52] U.S. Cl. ........................................ 356/71; 378/23
[58] Field of Search ............................. 356/71; 378/23

[56] References Cited

U.S. PATENT DOCUMENTS 4,246,483  1/1981  Weiss et al. ........................... 378/23

FOREIGN PATENT DOCUMENTS 2431700  2/1976  Fed. Rep. of Germany .
2746035  4/1979  Fed. Rep. of Germany .

OTHER PUBLICATIONS

Chu, D. C., et al. "Multiemulsion On–Axis Computer Generated Hologram," *Applied Optics.* vol. 12, No. 7, pp. 1386–1388 (Jul. 1973).

*Primary Examiner*—Vincent P. McGraw
*Attorney, Agent, or Firm*—Marc D. Schechter

[57] ABSTRACT

An apparatus for generating images of layers of an object from perspective images recorded from different positions by an array of radiation sources. The apparatus comprises an illumination device, for transilluminating the perspective images, and an imaging matrix comprising imaging elements. An optical system axis extends perpendicularly through the center of the matrix. The matrix superimposes the perspective images on a light-sensitive detector surface. In the apparatus, an optical deflection element is arranged in front of or behind each imaging element. The deflection element blurs the perspective image along a pattern which exhibits a major direction. The relevant deflection element is so arranged that the major direction extends at least substantially perpendicularly to a straight line connecting the optical system axis to the center of the imaging element within the matrix plane. All deflection elements are arranged in such a way relative to each other that the major directions subtend substantially equal angles with each other.

19 Claims, 8 Drawing Figures

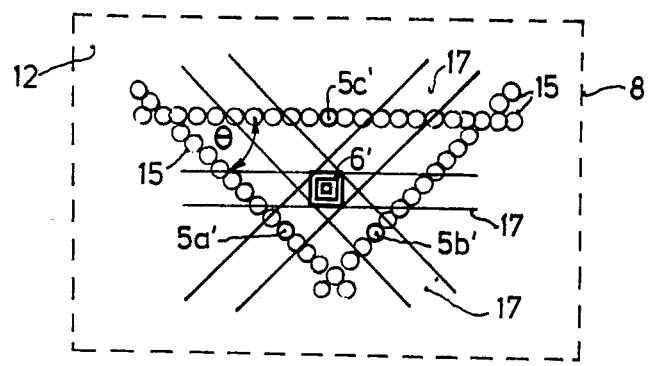
Fig. 4
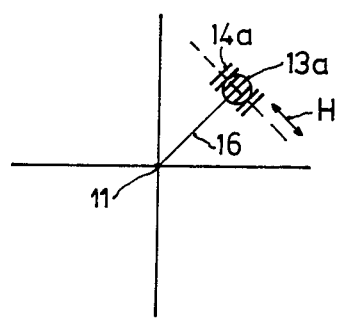
Fig. 5
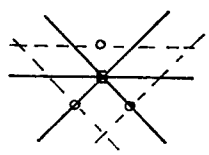 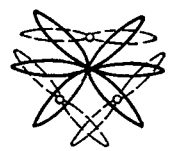 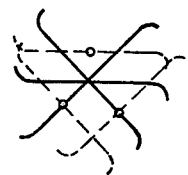
Fig.6a  Fig.6b  Fig.6c

SHORT-EXPOSURE TOMOSYNTHESIS APPARATUS FOR THE FORMATION OF LAYER IMAGES WITH A LOW ARTEFACT-CONTENT

BACKGROUND OF THE INVENTION

The invention relates to an apparatus for the forming images of a layer of an object. The layer images are formed from perspective images recorded from different positions by an array of radiation sources. The apparatus comprises an illumination device for transilluminating the perspective images, and an imaging matrix. The imaging matrix comprises imaging elements. An optical system axis extends perpendicularly through the center of the matrix. The imaging matrix is used for superimposing the perspective images on a light-sensitive detector surface.

Such an apparatus is generally known, for example, from German Pat. No. 27 46 035. Layer images obtained by using this apparatus are afflicted with artefacts because of the limited number of radiation sources or projection directions available in short-time tomosynthesis.

In principle the reconstructed layer image may exhibit two types of artefacts. First are those which arise during autocorrelation (shifting and adding, see German Offenlegungsschrift No. 24 31 700.8) of the perspective images representing the layer plane and which are caused by the perspective images themselves. Second are those caused by perspective images of other layers projected into the layer image.

SUMMARY OF THE INVENTION

It is an object of the invention to reduce those artefacts in the layer image which are produced by the projection of perspective images of other layers into the layer image.

According to the invention this problem is solved in that in front of or behind each imaging element there is arranged an optical deflection element. Each optical deflection element blurs the perspective image according to a pattern having one major direction. Each deflection element is so arranged that the major direction is at least substantially perpendicular to a straight line in the matrix plane which extend from the optical system axis to the center of the imaging element. All deflection elements so are arranged relative to each other that the major directions subtend substantially equal angles with respect to each other.

By thus arranging deflection elements in the radiation path between the imaging elements and the detector surface, the perspective images which represent object layers other than that layer desired to be imaged are blurred in such a way that a substantially uniform image background is obtained for the object structures in the reproduced layer. Thus, the structure of the image background is blurred to enhance the perceptibility of details in the actual object structures. The object structures situated in the reproduced layer plane are also blurred, but as a result of the special arrangement of the deflection elements relative to each other in the layer image this has no adverse effect, as will be explained in more detail hereinafter.

The deflection elements used according to the invention are optical elements which change the phase of the incident light, enabling the perspective images on the detector surface to be blurred in an advantageous manner.

Suitably the deflection elements are kinoforms (see, for example, Applied Optics, Volume 12, Number 7, pages 1386-1388 (July 1973)), holograms, or conventional optical gratings (for example line gratings). The perspective images deflected by the grating-like structures (for example in the kinoforms or holograms) are then situated on straight lines. Consequently, the major direction of the relevant deflection pattern then coincides with the direction of the straight line.

By means of further suitable kinoforms or holograms it is alternatively possible to deflect the perspective images according to other patterns, for example elongate curved paths, ellipses or the like. Then, the major direction of a pattern is that direction which corresponds to the greatest length of the pattern.

BRIEF DESCRIPTION OF THE DRAWING

FIG. 4 schematically represents a part of a reconstructed layer image with blurred artefacts.

FIG. 5 is a schematic plan view of an imaging matrix.

FIGS. 6a, 6b, and 6c shows different patterns for blurring the artefacts.

DESCRIPTION OF THE PREFERRED EMBODIMENTS

Figure 1:
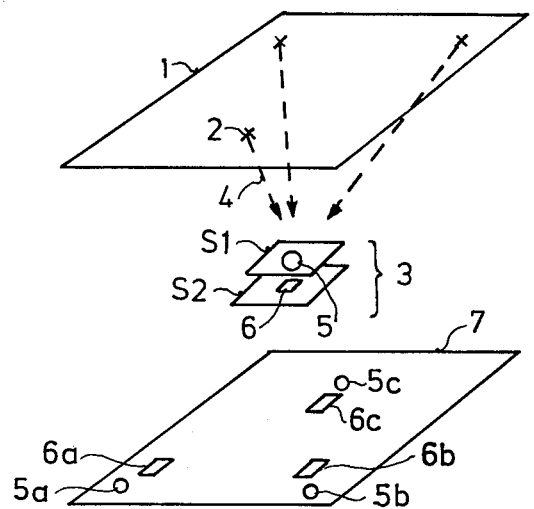
FIG. 1 schematically shows an apparatus for recording perpective images of an irradiated object.

FIG. 1 schematically shows a known short-time tomosynthesis apparatus. It comprises a plurality of radiation sources 2, for example X-ray tubes, which are arranged in a radiation-source plane 1. Only three sources are shown for the sake of clarity. The radiation sources 2 may be switched on, for example, consecutively or simultaneously. Underneath the radiation source plane 1 an object 3 to be examined is disposed. Object 3 is irradiated from different perspectives by the radiation beams 4, which are emitted by the radiation sources 2. Beams 4 may be stopped down by means of diaphragms (not shown).

For simplicity it is assumed that the object 3 comprises only two object layers S1 and S2. The object layer S1 contains, for example, a circle 5. The object layer S2 contains a square 6. The perspective images 5a-5c and 6a-6c produced by the object structures 5 and 6 are recorded, either separately or superimposed, on a record carrier 7, for example an X-ray film, disposed underneath the object 3.

Figure 2:
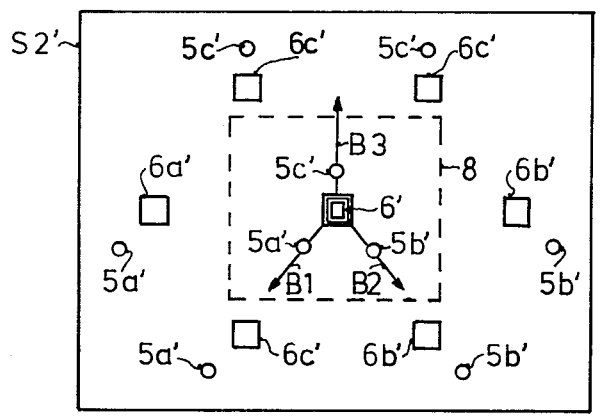
FIG. 2 schematically represents a layer image reconstructed from the recorded perspective image.

If, for example, the object layer S2 is to be reconstructed from the perspective images 5a-5c and 6a-6c thus recorded, the perspective images 6a-6c should be superimposed by appropriate shifting and should be added to each other (autocorrelation of the perspective images). However, all the other perspective images 5a-5c are then also shifted. The layer image S2' of the object layer S2 shown in FIG. 2 is then obtained.

In its center, the layer image S2' contains the square 6', reconstructed from the superimposed perspective images 6a-6c. Image S2' also contains a plurality of square secondary images 6a', 6b', 6c', which correspond to the perspective images 6a-6c. The perspective images 6a', 6b', 6c', which represent the object layer S2, form one group of artefacts in the layer image S2'.

In addition, the layer image S2' contains the circular perspective images 5a'–5c', which correspond to the prespective images 5a-5c. They form a second group of artefacts in the layer image S2'. The perspective images 5a'–5c', however, do not represent the object layer S2, but the object layer S1. They are perspective images of other object layers projected into the layer image.

When considering the circular artefacts 5a'–5c' in FIG. 2, they may again be divided into two sub-groups. These sub-groups are (i) artefacts situated near the center of the layer image S2' (within the dashed border 8), and (ii) artefacts situated near the image periphery (outside the border 8). In principle, these two sub-groups differ in that the perspective images 5a', 6a'; 5b', 6b'; 5c', 6c' which are situated within the border 8 are generated in pairs by imaging the perspective images 5a, 6a; etc. by means of their associated optical imaging elements. On the other hand, a perspective image 5a' situated outside the border 8 is, for example, generated by the optical elements associated with the perspective images 5b, 5c etc. This is shown in more detail in FIG. 3.

In order to improve the quality of the reconstructed layer images S2' the perspective images 5a'–5c', or artefacts, situated within the frame 8 are blurred. For this reference is made to FIG. 3, which represents an apparatus for reconstructing such enhanced layer images.

Figure 3:
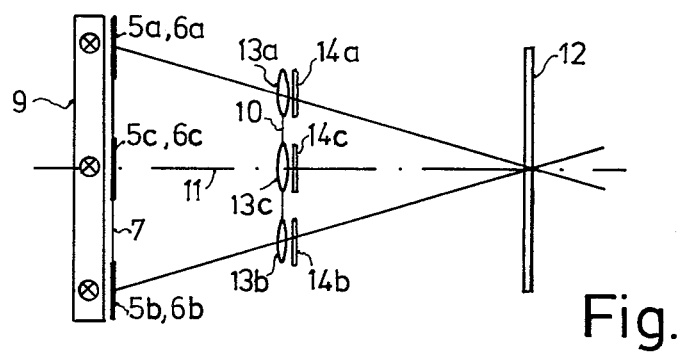
FIG. 3 schematically shows an apparatus for reconstructing of layer images.

The apparatus of FIG. 3 comprises a light box 9 for transilluminating of the perspective images 5a and 6a, 5b and 6b, and 5c and 6c on the record carrier 7 arranged in front of the box. A superimposed image of the perspective images is formed on a detector surface 12 by means of an imaging matrix 10, which is disposed parallel to the record carrier 7. An optical axis 11 extends perpendicularly through the center of matrix 10. For this purpose the imaging matrix 10 comprises separate imaging elements 13a–13c, for example biconvex lenses. Each lens is associated with a perspective image 5a and 6a, etc. In this way layer images of the object, which correspond to the layer image S2' shown in FIG. 2, are formed on the detector surface 12, for example a ground-glass screen or the entrance face of an optoelectronic image processing system.

When the perspective images 5a-5e are transmitted by their associated imaging elements 13a–13c (i.e. 5a with 13a, 5b with 13b and 5c with 13c), the artefacts 5a'–5c' situated within the border 8 in FIG. 2 are produced. However, when they are transmitted by nonassociated imaging elements (i.e. 5a with 13b and 13c, 5b with 13a and 13c, and 5c with 13a and 13b, the artefacts 5a'–5c' are formed outside the border 8.

In order to blur the perspective images 5a'–5c' situated inside the border 8 in FIG. 2, optical deflection elements 14a–14c are arranged in the radiation paths between the imaging elements 13a–13c and the detector surface 12, in the vicinity of the imaging elements 13a–13c. The deflection elements 14a–14c may blur the perspective images 5a-5c along, for example, straight paths. For this purpose, they have grating-like structures. Alternatively, the deflection elements 14a–14c may be arranged in the radiation paths between the perspective images 5a-5c and 6a-6c and the deflection elements 13a–13c.

Blurring will now be explained in more detail with reference to FIG. 4, which represents the area of the layer image S2' within the border 8 on an enlarge scale. This is the relevant area of the layer image S2', because only in this area are enough perspective images superimposed for the reconstructing images of object layers.

The layer image area outside the border 8 is generally not considered because here the perspective images are superimposed inadequately or not at all.

In FIG. 4 the perspective images 5a'–5c' are blurred along straight lines 15, that is, according to patterns having one major direction (in this case the directions of the straight lines). The grating-like deflection elements 14a–14c are then so arranged in the radiation paths that the major directions of the patterns formed as a result of the light deflection are substantially perpendicular to the paths B1, B2, B3 (FIG. 2). Paths B1, B2, and B3 are those paths along which the artefacts or perspective images 5a'–5c' travel over the detector surface when the detector 12 is moved along the optical axis 11 in order to reconstruct different layers of the object 3.

Thus, the major directions H, as shown in FIG. 5 projected onto a plan view of the matrix surface, are substantially perpendicular to a connecting line 16 between the optical axis 11 of the imaging matrix and the center of the respective imaging element 13a–13c in the matrix plane. For the sake of clarity, FIG. 5 shows only one imaging element 13a in the matrix plane (plane of the drawing). The deflection element 14a shown is an optical grating.

Such an arrangement of the deflection elements 14a–14c is advantageous, because the perspective images 5a'–5c' which are blurred along the straight line 15 (FIG. 4) cannot disturb the image of the reconstructed object structure 6'.

Moreover, in order to obtain a substantially uniform image background, it is necessary to distribute as uniformly as possible the directions along which the perspective images 5a'–5c' are blurred within the layer image S2'. Therefore, the angles $\theta$ between every pair of straight lines 15 should be substantially equal.

This arrangement of the deflection elements 14a–14c ensures that in comparison with the actual object structure 6' (which corresponds to the superposition of the perspective images 6a', 6b', 6c') the artefacts 5a'–5c' are attenuated. The attenuation of the artifacts enhances the perceptibility of details in the actual object structure 6'.

By means of the deflection elements 14a–14c the object structure 6', comprising the superimposed perspective images 6a'–6c', is also blurred along straight lines 17, which extend parallel to the straight lines 15. However, this does not significantly affect the quality of the layer images S2' because in the common area where all of the straight lines 17 are superimposed, the object structure 6' is imaged more frequently than outside the superposition area. Therefore, with a large number of straight lines 17 the observer will have the impression that the reconstructed object structure 6 is concentrated only in the area where the straight lines 17 are superimposed.

As already stated, the deflection elements 14a–14c comprise optical elements which change the phase of the incident light. The elements may, for example, be holograms or kinoforms, which may for example act as diffraction gratings. However, as an alternative an optical line grating may be employed. The gratings may be nonperiodical, for example in the kinoforms, so that the radiation distribution will be as uniform as possible in a preselected deflection range. The light box 9 may, for example, emit quasi-monochromatic radiation, for example the light from a sodium-vapor lamp. However, it may also emit polychromatic radiation, for example white light.

Furthermore, it is simple to obtain phase patterns by means of kinoform or holograms, by means of which patterns the transmitted perspective images are deflected or blurred along two-dimensional paths. FIGS. 6b and 6c show two examples of this deflection, while FIG. 6a again illustrates blurring according to FIG. 4. The continuous lines in FIGS. 6a and 6c represent the blurring paths of the object structure 6', while the broken lines represent the blurring paths of the perspective images 5a'–5c'. The major directions of the paths are those along which the paths extend over the greatest length. Moreover, it will be appreciated that blurring of the perspective images 5a'–5c' may alternatively be effected along different paths.

In an advantageous embodiment of the invention each imaging element and each deflection element are combined to form a single optical element which changes the phase of the incident light. The elements 13a–14a, 13b–14b and 13c–14c may then, for example, be replaced by a single kinoform or a single hologram.

What is claimed is:

1. An apparatus for forming images of a layer of an object from perspective images recorded by an array of radiation sources at different positions, said apparatus comprising:
   an illumination device for emitting light, said device being arranged to pass light through the recorded perspective images;
   a detector having a light-sensitive surface; and
   a planar imaging matrix arranged to be illuminated by the light from the illumination device which passes through the recorded perspective images, said matrix comprising a plurality of imaging elements having centers, said matrix having a center and an optical axis extending through the center of the matrix perpendicular to the matrix plane, said matrix functioning, in operation, to form superimposed images of the recorded perspective images on the detector surface;
   characterized in that the apparatus further comprises a plurality of deflection elements, each deflection element being arranged in front of or behind a corresponding imaging element, each deflection element functioning to blur the image formed by its corresponding imaging element, said blur being in a pattern having one major direction, each deflection element being arranged so that the major direction projected onto the matrix plane is substantially perpendicular to a straight line between the optical axis of the imaging matrix and the center of the corresponding imaging element, each imaging element being arranged so that the major directions of the deflection elements subtend substantially equal angles with respect to each other.

2. An apparatus as claimed in claim 1, characterized in that the deflection elements are optical elements which change the phase of light incident thereon.

3. An apparatus as claimed in claim 2, characterized in that the deflection elements are kinoforms.

4. An apparatus as claimed in claim 2, characterized in that the deflection elements are holograms.

5. An apparatus as claimed in claim 2, characterized in that the deflection elements are optical gratings.

6. An apparatus as claimed in claim 5, characterized in that each grating has a nonperiodic structure.

7. An apparatus as claimed in claim 2, characterized in that each deflection element blurs the image formed by its corresponding imaging element in a two-dimensional pattern.

8. An apparatus as claimed in claim 2, characterized in that each deflection element is arranged between its corresponding imaging element and the surface of the detector.

9. An apparatus as claimed in claim 2, characterized in that each deflection element and its corresponding imaging element are combined into one optical element.

10. An apparatus as claimed in claim 2, characterized in that the illumination device emits quasi-monochromatic light.

11. An apparatus as claimed in claim 1, characterized in that each deflection element is arranged between its corresponding imaging element and the surface of the detector.

12. An apparatus as claimed in claim 1, characterized in that each deflection element and its corresponding imaging element are combined into one optical element.

13. An apparatus as claimed in claim 1, characterized in that the illumination device emits quasi-monochromatic light.

14. An apparatus for forming images of a layer of an object from perspective images recorded by an array of radiation sources at different positions, said apparatus comprising:
   an illumination device for emitting light, said device being arranged to pass light through the recorded perspective images;
   a detector having a light-sensitive surface; and
   a planar imaging matrix arranged to be illuminated by the light from the illumination device which passes through the recorded perspective images, said matrix comprising a plurality of imaging elements having centers, said matrix having a center and an optical axis extending through the center of the matrix perpendicular to the matrix plane, said matrix functioning, in operation, to form superimposed images of the recorded perspective images on the detector surface;
   characterized that the apparatus further comprises a plurality of deflection elements, each deflection element being arranged in front of or behind a corresponding imaging element, each deflection element functioning to blur the image formed by its corresponding imaging element, said blur being in a pattern having one major direction, each deflection element being arranged so that the major direction projected onto the matrix plane crosses a straight line between the optical axis of the imaging matrix and the center of the corresponding imaging element, each imaging element being arranged so that the major directions of the deflection elements are distributed as uniformly as possible around the optical axis of the imaging matrix.

15. An apparatus as claimed in claim 14, characterized in that the deflection elements are optical elements which change the phase of light incident thereon.

16. An apparatus as claimed in claim 15, characterized in that each deflection element blurs the image formed by its corresponding imaging element in a two-dimensional pattern.

17. An apparatus as claimed in claim 15, characterized in that each deflection element is arranged between its corresponding imaging element and the surface of the detector.

18. An apparatus as claimed in claim 15, characterized in that each deflection element and its corresponding imaging element are combined into one optical element.

19. An apparatus as claimed in claim 15, characterized in that the illumination device emits quasi-monochromatic light.

* * * * *